United States Patent
Leshner

(10) Patent No.: US 11,191,450 B1
(45) Date of Patent: Dec. 7, 2021

(54) RE-BREATHING ANALYZER

(71) Applicant: Michael David Leshner, Elkton, MD (US)

(72) Inventor: Michael David Leshner, Elkton, MD (US)

( * ) Notice: Subject to any disclaimer, the term of this patent is extended or adjusted under 35 U.S.C. 154(b) by 0 days.

(21) Appl. No.: 17/366,929

(22) Filed: Jul. 2, 2021

Related U.S. Application Data

(60) Provisional application No. 63/050,761, filed on Jul. 11, 2020.

(51) Int. Cl.
| | | |
|---|---|---|
| *A61B 5/087* | (2006.01) | |
| *G01N 33/36* | (2006.01) | |
| *G01N 1/22* | (2006.01) | |
| *G01K 13/024* | (2021.01) | |

(52) U.S. Cl.
CPC .......... *A61B 5/0878* (2013.01); *G01K 13/024* (2021.01); *G01N 1/22* (2013.01); *G01N 33/367* (2013.01); *G01N 2001/2244* (2013.01)

(58) Field of Classification Search
CPC ................. G01N 33/367; G01N 1/22; G01N 2001/2244; G01K 13/024; A61B 5/0878
See application file for complete search history.

(56) References Cited

U.S. PATENT DOCUMENTS

| | | | | |
|---|---|---|---|---|
| 2003/0191405 | A1* | 10/2003 | Rich ...................... | A61B 5/097 600/532 |
| 2014/0013825 | A1* | 1/2014 | Liu ..................... | G01N 15/0826 73/38 |

OTHER PUBLICATIONS

Patrick L. Carolan et al., Potential to Prevent Carbon Dioxide Rebreathing of Commercial Products Marketed to Reduce Sudden Infant Death Syndrome Risk, PPediatrics vol. 105 No. Apr. 4, 2000 (Year: 2000).*

Forensic Engineering Evaluation of CO2 Re-Breathing in Infant Bedding Materials, by Michael Leshner, P.E., Journal of the National Academy of Forensic Engineers, vol. XXIX No. 2, Dec. 2012, pp. 23-30.

Mechanical Model Testing of Rebreathing Potential in Infant Bedding Materials, by Carlton, Donoghue, & Porter; Archives of Disease in Childhood 1998; 78:323-28.

Carbon Dioxide Rebreathing Induced by Crib Bumpers and Mesh Liners Using an Infant Manikin, Matthew R. Maltese & Michael Leshner, BMJ Paediatrics Open, bmjpo-000374, Apr. 2019.

* cited by examiner

*Primary Examiner* — Marrit Eyassu
(74) *Attorney, Agent, or Firm* — Knox Patents; Thomas A. Kulaga

(57) ABSTRACT

Apparatus for quantifying the amount of re-breathing due to bedding materials. The re-breathing analyzer applies heated air to the material under test through an exhaust port in a probe and receives return air from an intake port in the probe. The exhaust and intake ports are placed to engage the material under test when the probe is in contact with the material. In one embodiment, the probe has a surface that is exposed through a top surface of a housing for the analyzer whereby the material under test is placed on the top surface for testing. The analyzer includes a differential temperature measuring instrument that determines the temperature of the return air, where an increase of the temperature of the return air above the temperature of the ambient air indicates the presence and quantity of re-breathing due to the material under test.

20 Claims, 6 Drawing Sheets

RE-BREATHING ANALYZER

CROSS-REFERENCE TO RELATED APPLICATIONS

This application claims the benefit of U.S. Provisional Application No. 63/050,761, filed Jul. 11, 2020.

STATEMENT REGARDING FEDERALLY SPONSORED RESEARCH OR DEVELOPMENT

Not Applicable

BACKGROUND

1. Field of Invention

This invention pertains to a re-breathing analyzer. More particularly, this invention pertains to a device that measures air temperature to determine if a material under test is susceptible to re-breathing of carbon dioxide by an infant.

2. Description of the Related Art

Infants placed on mattresses and other bedding need access to fresh air. Unfortunately, some bedding materials contribute to re-breathing by the infant on the bedding, particularly when the infant is stomach sleeping. Stomach sleeping is when an infant is sleeping or positioned with the infant's frontal plane facing the bedding, that is, the infant is prone, which is lying with the stomach adjacent the bedding, and not supine, which is lying face upward with the stomach away from the bedding.

Re-breathing occurs when an infant breathes in a portion of his or her own exhaled air. Soft bedding or stuffed toys and/or pillows or other bedding near the infant's face can contribute to re-breathing. Re-breathing is an issue for infants because as the infant breaths in exhaled air, the infant's oxygen levels are reduced and the level of carbon dioxide ($CO_2$) in the body increases. In extreme cases in which the infant does not wake and cry out or cannot change position, suffocation can result from re-breathing.

Under normal circumstances, when a human, such as an infant, breathes out, carbon dioxide from the body's natural processes is exhausted with each exhalation. The increased concentration of carbon dioxide in the exhaled breath is normally dissipated in the air, and when that infant then breathes in, the infant receives ambient air with its normal, naturally occurring minimal concentration of carbon dioxide. If the infant's exhaled breath does not fully dissipate before the infant inhales, re-breathing occurs. The extent of re-breathing depends upon how much the exhaled breath dissipates by mixing with the surrounding air before the subsequent inhalation. As the infant inhales air with an increased concentration of carbon dioxide, the infant's body concentration of carbon dioxide increases and the concentration of carbon dioxide in subsequent exhalations increases. In this way, a positive feedback loop is created.

Normally, an infant will wake, cry out, and/or change position when the infant experiences a high level of carbon dioxide in the body. But not always, and in those cases, as the breathing cycle repeats and continues, the concentration of carbon dioxide ($CO_2$) in the blood rises to hazardous and possibly deadly levels. Carbon dioxide re-breathing ($CO_2RB$) is believed to be one of the causes of sudden infant death syndrome (SIDS).

Some bedding materials capture and store a portion of the exhaled breath, preventing the exhaled breath from dissipating into the ambient air, and that captured breath can be then inhaled. It is desirable to test bedding materials to determine if the bedding material is susceptible to capturing and storing exhaled breath, thereby leading to re-breathing. Conventional methods of testing bedding materials use a mechanical breathing device that delivers a known concentration of carbon dioxide gas to the bedding material under test and then measuring the concentration of carbon dioxide received by the device. In such devices, carbon dioxide is metered into a mechanically actuated lung and exhausted from an infant model into the material under test with each exhaled breath. The mechanically actuated lung draws in air from the material under test and the level of carbon dioxide is measured using a $CO_2$ analyzer. The level of measured carbon dioxide determines the amount of re-breathing due to the material under test. Conventional carbon dioxide devices are calibrated using reference gases under repeatable conditions of breathing frequency, tidal volume, and dead space volume. In order to achieve reliable and repeatable measurements, an operator with a high level of expertise and experience is required, along with complex and often expensive equipment, such as the carbon dioxide analyzer.

BRIEF SUMMARY

According to one embodiment of the present invention, a re-breathing analyzer is provided. The re-breathing analyzer applies heated air through a supply line or conduit to the material under test, and monitors the temperature of air returned from the material under test through a return line or conduit. The temperature of the return line is a proxy for the carbon dioxide resulting from re-breathing associated with the material under test. By using heated air and measuring the temperature of the return air, the need for carbon dioxide gas and sensitive and complex carbon dioxide analyzers is eliminated. Just as certain bedding materials store exhaled carbon dioxide, the same is true for exhaled heated air. The extent of re-breathing is determined by the difference between the inhaled breath temperature and a reference temperature. That is, there is no re-breathing if the temperature of the return air is the same as the temperature of the ambient air and there is 100% re-breathing if the temperature of the return air is the same as the temperature of the heated air.

The re-breathing analyzer includes a heated air supply directed to the material under test and a return air line from the material under test. The heated air supply, the return air, and the ambient air all have an associated temperature. The temperature of the return air falls between a high of the heated air supply temperature and a low of the ambient air temperature. The closer the return air temperature is to the ambient air temperature, the less re-breathing there is due to the material under test. If the return air temperature equals the ambient air temperature, there is no re-breathing. The closer the return air temperature is to the heated air temperature, the more re-breathing there is due to the material under test. If the return air temperature equals the heated air temperature, there is 100 percent re-breathing. In one embodiment, the analyzer measures the differential temperature between the return air and the ambient air. In another embodiment, the analyzer measures the differential temperature between the return air and the heated air. In one embodiment, a thermocouple pile measures the differential temperature, with the output of the thermocouple pile connected to a fixed gain amplifier that provides an output corresponding to the differential temperature.

The re-breathing analyzer has an embodiment that operates in a unidirectional, continuous mode and another embodiment that operates in a bi-directional mode. The unidirectional embodiment includes an air pump with the discharge connected to a heater that continuously provides heated air to a probe that interfaces with the material under test. The heater is controlled to ensure a constant temperature is exhausted through the probe. The inlet to the air pump is connected to a return line that sucks air from the probe. In one embodiment, the inlet is also connected to a suction line that receives ambient air. In such an embodiment, the return line and the ambient air suction line each contain a temperature sensor.

The bi-directional embodiment includes a bi-directional pump, such as a mechanical lung, with an output connected to a heater. The heater has an output connected to a supply line and a return line, both terminating at a probe that interfaces with the material under test. The supply line has a supply check valve and a supply temperature sensor. The supply check valve insures that heated air is directed from the pump to the probe. The return line has a return check valve and a return temperature sensor. The return check valve insures that return air is directed from the probe to the pump.

The interface between the re-breathing analyzer and the material under test is a probe that includes an exhaust port of heated air and an intake port of return air, with both ports positioned adjacent each other such that the ports are in close proximity or contact with the material under test. In one embodiment, the two ports are separated by approximately one inch distance. The probe, in various embodiments, includes the differential temperature sensors or the differential temperature sensors and the amplifier.

In various embodiments, the probe has various shapes and ways of interfacing with the material under test. In one embodiment, the probe has a disc-shape that has one surface exposed through a housing. During a re-breathing test, the material under test is positioned in contact with the exposed surface of the probe and the housing. The housing contains the air circulation equipment and the heater. In one such embodiment, the housing also contains associated controls and outputs or displays.

In another embodiment, the probe has a disc-shape that is attached to a mechanism that positions the probe to engage the material under test. In yet another embodiment, the probe has a hemispherical-type shape that is attached to a mechanism that positions the probe to engage the material under test.

BRIEF DESCRIPTION OF THE SEVERAL VIEWS OF THE DRAWINGS

The above-mentioned features will become more clearly understood from the following detailed description read together with the drawings in which.

DETAILED DESCRIPTION

Apparatus for a re-breathing analyzer 100 is disclosed. The analyzer is generally indicated as 100, with particular embodiments and variations shown in the figures and described below having an alphanumeric suffix, for example, 100-A, 100-B, 100-1, 100-2. Various components are illustrated both generically and specifically in the figures and in the following description. For example, the various embodiments of the probe 102-A, 102-B are discussed individually and separately to ensure clarity when describing the specific configuration of each probe 102-A, 102-B. The probe 102, when referred to generally and collectively without regard to the differences between the embodiments, is referenced without the alphanumeric suffix. Furthermore, directional references, for example, top and bottom, are in reference to the deployed orientation of the component, such as the probe 102-A, 102-B, under discussion.

Figure 1:
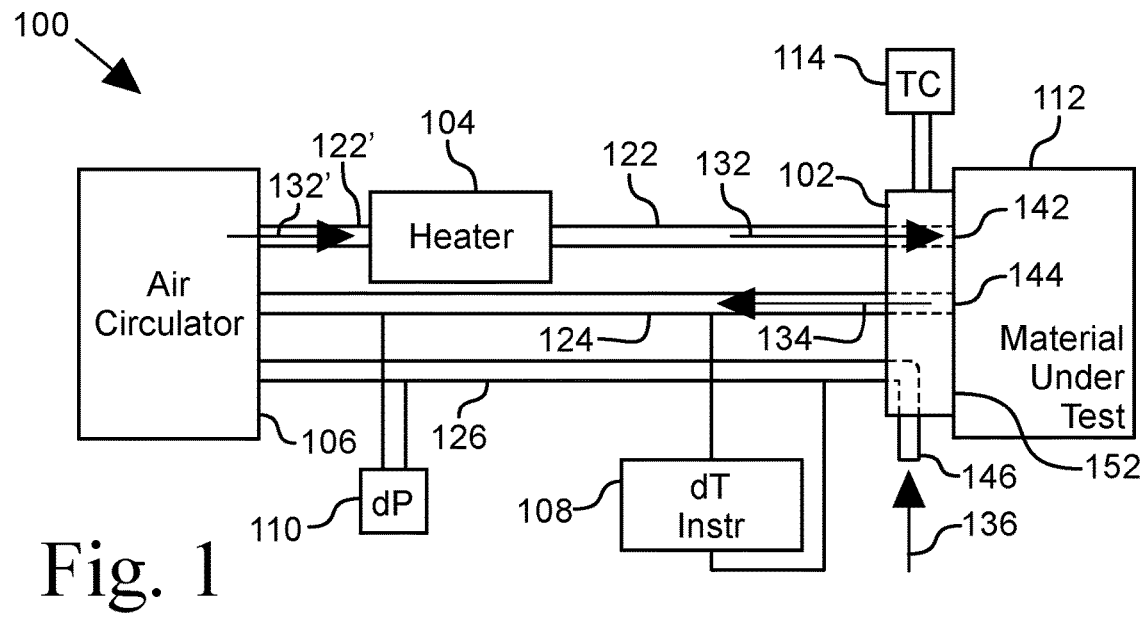
FIG. 1 is a block diagram of one embodiment of a re-breathing analyzer.

FIG. 1 illustrates a block diagram of one embodiment of a re-breathing analyzer 100. The analyzer 100 includes a probe 102, a heater 104, a heated air conduit 122, an air circulator 106, a return air conduit 124, an ambient air conduit 126, and a differential temperature instrument (dT Instr) 108. The probe 102 engages the material under test 112. The material under test 112 is generally some type of bedding material, such as used by infants and toddlers. The material under test 112 includes mattresses and sleeping pads or other soft materials used in children's products. The analyzer 100 provides for repeatable testing of such bedding material during manufacturing and certification to ensure that the bedding material does not present a re-breathing hazard to humans, such as infants.

In the illustrated embodiment, the air circulator 106 pushes air 132' through the heater 104 where it becomes heated air 132. The heated air 132 flows to the probe 102, through the exhaust port 142, and to the material under test 112. The air circulator 106 pulls or draws the return air 134 from the intake port 144 in the face 152 of the probe 102. The air circulator 106 also pulls or draws the ambient air 136 from the area around the probe 112. In various embodiments, the air circulator 106 includes one or more air pumps 206, a mechanical lung or reciprocating cylinder 306, and/or one or more fans 506 and air vents 516.

The probe 102 provides the interface between the other parts of the analyzer 100 and the material under test 112. The analyzer 100 is configured so that an outer surface 152 of the probe 102 is positionable in close proximity or in contact with the material under test 112 with a preselected force. The outer, or contact, surface 152 of the probe 102 has two ports, an exhaust port 142 and an inlet port 144, that are proximate the material under test 112. In one embodiment, the probe 102 is made of a material that has low thermal conductivity. That is, the material of the probe 102 acts as a thermal insulator with a low amount of heat conduction. Examples of such material include wood and some polymers. The thermal conductivity of the probe 102 is such that the probe 102 is minimally susceptible to changes in temperature due to the heated air 132 flowing through the probe 102. In this way, the return air 134 from the intake port 144 reflects the temperature of the air received at the intake port 144 without being influenced unduly by the temperature of the heated air 132 flowing through the body of the probe 102.

In the illustrated embodiment, a temperature controller (TC) 114 engages the probe 102. The temperature controller 114 controls the temperature of the probe 102. In one such embodiment, the temperature of the probe 102 is maintained at a specified temperature, as measured by temperature sensors in the probe 102 and in the ambient air 136. In another embodiment, the temperature controller 114 includes a thermoelectric temperature device that selectively cools and/or heats the probe 102, thereby ensuring that the temperature of the probe 102 remains stable and at the specified temperature. One such thermoelectric device uses the Peltier effect to control the temperature of the probe 102. In one embodiment, the specified temperature is ambient temperature. In another embodiment, the specified temperature is a temperature above ambient, for example, 2 to 10 degrees Celsius. In this way, the temperature of the probe 102 is maintained at a constant temperature, thereby ensuring the accuracy and repeatability of test results.

Heated air 132 flows in the heated air conduit 122 from the heater 104 to the probe 102 and to the material under test 112 through an exhaust port 142. Air 132', before becoming heated air 132, flows in a portion of the heated air conduit 122' between the air circulator 106 and the heater 104. The heater 104 heats the air 132' from the air circulator 106 to a temperature above that of the ambient air 136. The heater 104, in one embodiment, heats the heated air 132 to 98.6 degrees Fahrenheit. In one embodiment, the heater 104 heats the heated air 132 to the nominal temperature of the breath exhaled by a human infant.

Return air 134 flows in the return air conduit 124 from the probe 102 in contact with the material under test 112 to the air circulator 106. The probe 102 has an intake port 144 that is proximate the material under test 112. The intake port 144 is near the exhaust port 142. In one embodiment, the two ports 142, 144 are approximately one-eighth inch in diameter and one inch apart. The probe 102 is configured so that the material under test 112 is positionable against the two ports 142, 144 in the probe 102. In this way, the heated air 132 is directed out of port 142 and into the material under test 112 and the return air 134 is pulled through port 144 adjacent to the material under test 112.

Ambient air 136 flows in the ambient air conduit 126 from an ambient air port 146 located near the side of the probe 102, through the probe 102, and to the air circulator 106. The ambient air inlet port 146 is positioned proximate the probe 112 and in a location where the ambient air inlet port 146 is not susceptible to drawing in any heated air 132 exhausted from the exhaust port 142. In the illustrated embodiment, the ambient air 136 is pulled through the ambient air conduit 126 by the air circulator 106 with the differential temperature instrument 108 measuring the temperature of the ambient air 136 in the conduit 126. In another embodiment, the temperature of the ambient air 136 is measured in the open space around the probe 102. In one such embodiment, the air circulator 106 includes a fan 506 that circulates the ambient air 136 in the space around the ambient air inlet port 146, such as within the housing 502.

The temperature of the heated air 132 and the temperature of the ambient air 136 are substantially fixed. That is, the temperature of the heated air 132 is controlled to a fixed temperature by the heater 104 and the temperature of the ambient air 136 is generally unchanging over the time the analyzer 100 is in operation because the large volume of air surrounding the analyzer 100 and the material under test 112 acts as a heat sink. The temperature of the return air 134 varies between a high temperature and a low temperature. The high temperature corresponds to the temperature of the heated air 132 and the low temperature corresponds to the temperature of the ambient air 136. The point where the temperature of the return air 134 falls within this range corresponds to the amount of re-breathing due to the material under test 112.

In the illustrated embodiment, a differential pressure instrument 110 is connected to the return air conduit 124 and the ambient air conduit 126. The differential pressure instrument 110 measures the pressure difference between the pressure of the return air 134 in the return air conduit 124 and the pressure of the ambient air 136 in the ambient air conduit 126.

In the illustrated embodiment, a differential temperature instrument (dT Instr) 108 measures the difference in temperature between the return air 134 and the ambient air 136. When there is no re-breathing from the material under test 112, the temperature of the return air 134 is substantially equal to the temperature of the ambient air 136. As the amount of re-breathing from the material under test 112 increases, the temperature of the return air 134 approaches the temperature of the heated air 132. If the temperature of the return air 134 were to reach a temperature substantially equal to the temperature of the heated air 132, the amount of re-breathing would be 100%. In another embodiment, the differential temperature instrument (dT Instr) 108 measures the difference in temperature between the return air 134 and the heated air 132. In such an embodiment, the lower the differential temperature, the greater the re-breathing from the material under test 112.

Figure 2:
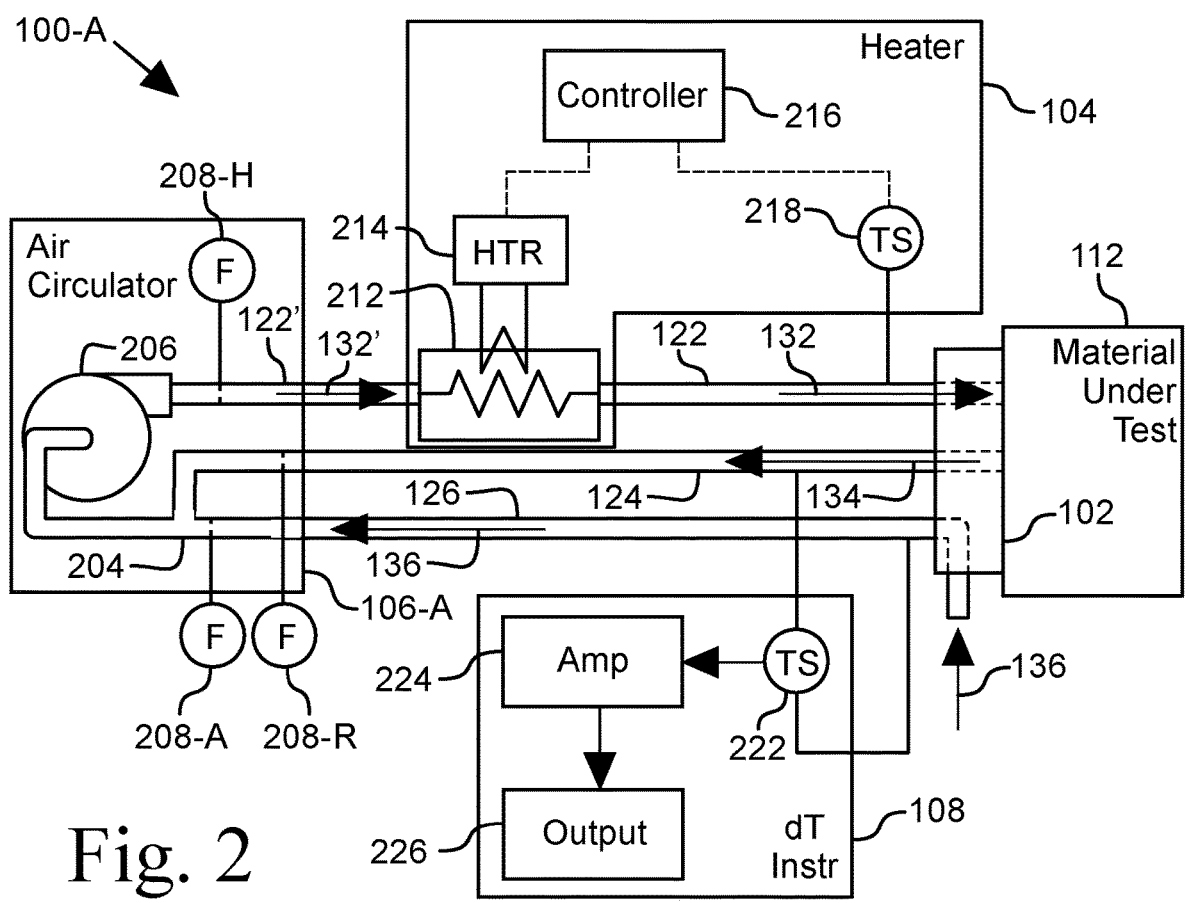
FIG. 2 is a system diagram of a unidirectional embodiment of a re-breathing analyzer.

FIG. 2 illustrates a system diagram of a unidirectional embodiment of a re-breathing analyzer 100-A. The unidirectional re-breathing analyzer 100-A continuously sends heated air 134 out the exhaust port 142 of the probe 102 and continuously receives return air 134 from the intake port 144.

The air circulator 106-A of the illustrated unidirectional embodiment of the re-breathing analyzer 100-A includes an air pump 206. The discharge or outlet of the air pump 206 is in fluid connection with the air conduit 122' that provides air 132' to the heater 104. The suction side of the air pump 206 is in fluid connection with a manifold 204 that is in fluid connection with the return air conduit 124 and the ambient air conduit 126. In one such embodiment, the air flow of heated air 132 is twice the flow of the return air 134 and twice the flow of the ambient air 136. In the illustrated embodiment, flow gages 208-H, 208-R, 208-A are shown on the various conduits 122', 124, 126 for measuring and controlling the flow for the heated air 132, the return air 134, and the ambient air 136. In one such embodiment, the heated air 132 has a flow rate of two liters per minute and the return air 134 and ambient air 136 each have a flow rate of one liter per minute. In another embodiment, the flow gages 208 are not used with the air flows determined by component and conduit selection.

The illustrated embodiment shows the heater 104 including a heat exchanger 212 through which the heated air flows, a heater element (HTR) 214 that provides heat to the heat exchanger 212, and a controller 216 connected to a temperature sensor 218. The controller 216 is responsive to the temperature sensor 218 that monitors the temperature of the heated air 132 flowing out of the probe 102. The controller 216 operates the heater element 214 to control the temperature of the heated air 132. In various embodiments, the temperature sensor 218 senses the temperature of the heated air 132 at some point between the outlet of the heat exchanger 212 and the exhaust port 142 in the probe 102. In one such embodiment, the temperature sensor 218 senses the temperature of the heated air 132 as it exits the exhaust port 142.

The differential temperature instrument (dT Instr) 108 includes a temperature sensor 222, an amplifier 224, and one or more output devices 226. The illustrated temperature sensor 222 is responsive to the temperature of the return air 134 relative to the temperature of the ambient air 136. The temperature sensor 222 produces an output that is received by the amplifier 224, which produces an output that is received by the one or more output devices 226. In another embodiment, the temperature sensor 222 is responsive to the temperature of the ambient air 136 as measured in the space adjacent the probe 102. In yet another embodiment, the temperature sensor 222 is responsive to the temperature of the return air 134 relative to the temperature of the heated air 132. The amplifier 224 is a device that converts the output of the temperature sensor 222 into a signal suitable for the output 226.

Figure 3:
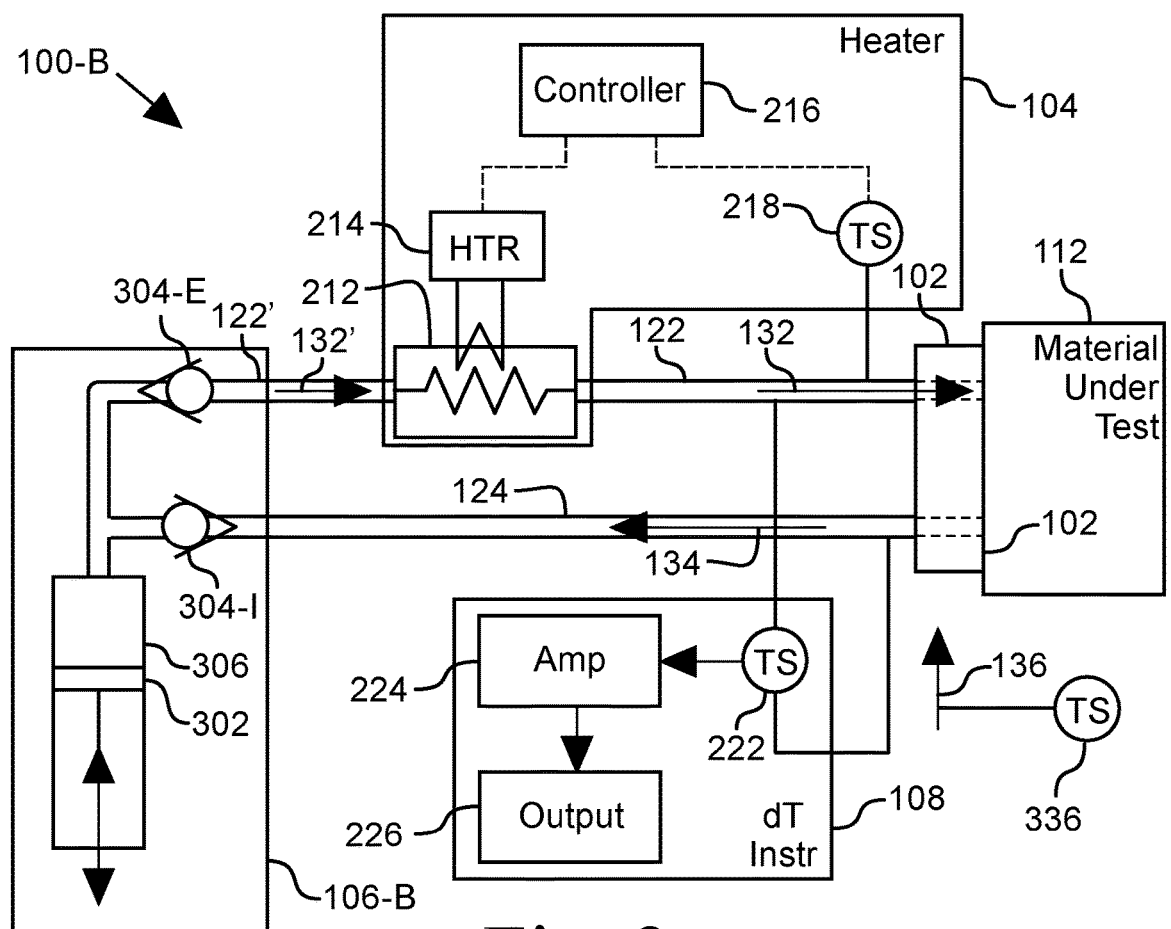
FIG. 3 is a system diagram of a bi-directional embodiment of a re-breathing analyzer.

FIG. 3 illustrates a system diagram of a bi-directional embodiment of a re-breathing analyzer 100-B. The bi-directional re-breathing analyzer 100-B includes an air circulator 106-B with a mechanical lung or reciprocating air cylinder 306 that simulates the breathing pattern of a human, such as an infant. That is, the cylinder 306 includes a bi-directional piston 302 that sequentially pushes heated air 132 out the exhaust port 142 of the probe 102 and pulls or draws return air 134 from the intake port 144. The cylinder 306 repeatedly pushes and pulls the air 132, 134. An exhaust check valve 304-E permits only the air 132', 132 to flow from the cylinder 306 through the heated air conduit 122', 122 to the probe 102. An intake check valve 304-I permits only the return air 134 to flow from the probe 102 to the cylinder 306. The flow rate of the heated air 132 and the return air 134 is determined by the volume of air moved by the air cylinder 306 and the rate of reciprocation of the piston 302 in the air cylinder 306, as impacted by the back pressure due to the properties of the material under test 112. In one embodiment, the volume of air moved by the air cylinder 306 is substantially the same volume as would be expected to be breathed by an infant.

The illustrated temperature sensor 222 is responsive to the temperature of the return air 134 relative to the temperature of the heated air 132. In another embodiment, temperature sensor 222 is responsive to the temperature of the return air 134 relative to the temperature of the ambient air 136. A separate temperature sensor (TS) 336 is illustrated as monitoring the temperature of the ambient air 136. In yet another embodiment, an ambient air conduit 126, such as shown in FIG. 2, is connected in parallel with the return air conduit 134 so that the ambient air 136 is pulled into the cylinder 306 through the intake check valve 304-I. In such an embodiment, the temperature sensor 222 is responsive to the temperature of the return air 134 relative to the temperature of the ambient air 136.

Figure 4:
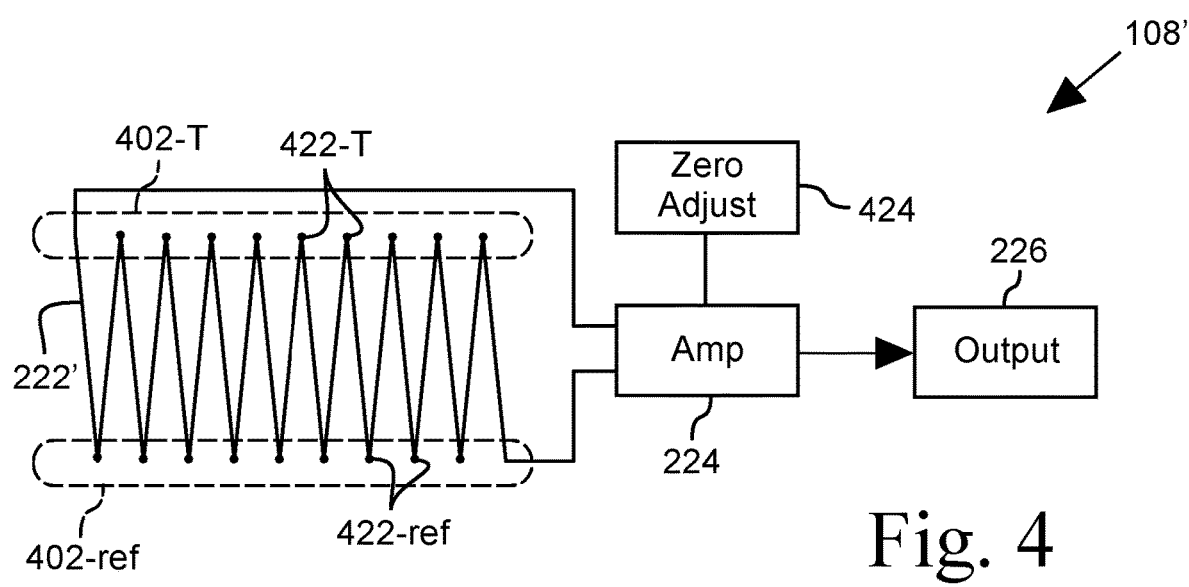
FIG. 4 is a schematic diagram of one embodiment of differential temperature circuit.

FIG. 4 illustrates a schematic block diagram of one embodiment of the differential temperature instrument circuit 108'. The illustrated embodiment of the differential temperature instrument 108' includes a temperature sensor 222 that is a thermopile 222', which is connected to an amplifier 224 that is connected to one or more output devices 226.

The illustrated thermopile 222' is a thermocouple with multiple, series connected pairs of junctions 422-T, 422-ref with the associated junctions 422-T, 422-ref in respective cavities 402-T, 402-ref. Each thermocouple junction 422-T, 422-ref generates a voltage dependent upon the temperature to which the junction 422-T, 422-ref is exposed. By series connecting the junctions 422-T, 422-ref the output voltage of the thermopile 222' is increased algebraically by the number of junctions 422-T, 422-ref. In the illustrated embodiment, there are ten pairs of junctions 422-T, 422-ref and the thermopile 222' output is ten times the voltage difference between each pair of junctions 422-T, 422-ref. Accordingly, small differences in temperature result in large increases in output voltage. In one such embodiment, the thermopile 222' includes multiple pair of junctions 422-T, 422-ref of Type E thermocouple wire, where each pair of pair of junctions 422-T, 422-ref produces 59 microvolts per degree Celsius at a differential temperature of 10 degrees Celcius for a total of 590 microvolts per degree when there are 10 pairs of junctions 422-T, 422-ref.

The amplifier 224 increases the output voltage of the thermopile 222'. In one embodiment, the amplifier 224 is a fixed-gain, differential amplifier with one or more stages. In such an embodiment, the amplifier 224 drives a standard millivoltmeter 226 displaying the output as a number. The fixed-gain amplifier 224 eliminates the need to calibrate the thermopile 22' and amplifier 224. In various embodiments, the amplifier 224 has a fixed gain in the range of 10 to 100 times, which increases the thermopile 222' output voltage to a level more suitable for the output device 226.

In the illustrated embodiment, a zero adjust 424 is associated with the amplifier 224. The zero adjust 424 operates on the amplifier 224 to compensate for changes in the ambient temperature. For isothermal conditions where the junctions 422-T, 422-ref of the thermopile 222' are exposed to the same temperature, the output of the amplifier 224 should be zero. But for situations where the output of the amplifier 224 is not zero when it should be, the zero adjust 424 allows for control of the amplifier 224 to bring the output to zero. In one embodiment, the zero adjust 424 changes the offset voltage setting of the amplifier 224, thereby adjusting the output of the amplifier 224 to zero when there is no material under test 112 present.

The output signal from the amplifier 224 is connected to an output 226. In various embodiments, the output 226 includes an analog display, a digital display, and/or a computer readable output for further processing, such as data logging, remote display, and/or data processing. Those skilled in the art will recognize that the output 226 is one or more devices that are suitable for the application in which the analyzer 100 is used without departing from the spirit and scope of the present invention.

FIG. 4 illustrates a simplified schematic of one embodiment of the differential temperature instrument circuit 108'. The simplified schematic does not illustrate various connections, for example, power and ground connections to the various components 222', 224, 424, 226; however, those skilled in the art will recognize the need for such wiring and understand how to wire such a circuit, based on the components ultimately selected for use. Furthermore, the simplified schematic does not illustrate other electrical components and connections, such as for the air circulator 106, heater 104, and associated components. Those skilled in the art will recognize what components are needed and how to connect, control, and power such components and devices without departing from the spirit and scope of the present invention.

Figure 5:
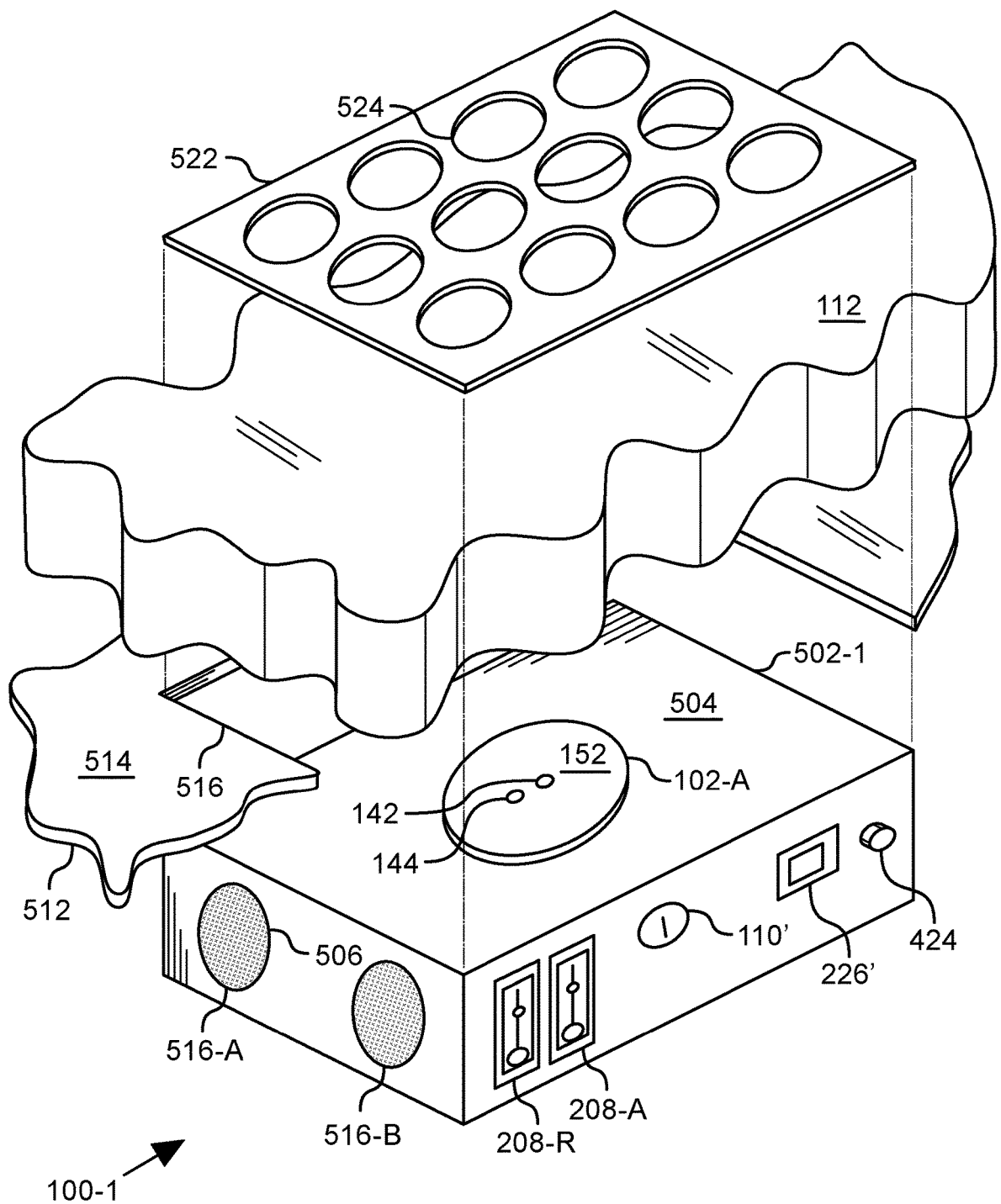
FIG. 5 is an exploded, isometric view of one embodiment of a re-breathing analyzer.

FIG. 5 illustrates an exploded, isometric view of one embodiment of a re-breathing analyzer 100-1 that is a self-contained unit. The illustrated analyzer 100-1, in various embodiments, is either a unidirectional embodiment of a re-breathing analyzer 100-A or a bi-directional embodiment of a re-breathing analyzer 100-B. The illustrated analyzer 100-1 includes a housing 502-1 with the contact surface 152 of the probe 102-A extending above the top surface 504 of the housing 502-1. The illustrated embodiment of the analyzer 100-1 also includes a pair of fans 506 on one side, a pair of flow gages 208-R, 208-A, a differential pressure gage 110', and a readout 226' on another side.

In the illustrated embodiment, the probe 102-A has a disc-shape with the top surface 152 of the probe 102-A protruding slightly above the top surface 504 of the housing 502-1. In such an embodiment, the slight protrusion ensures the probe 102-A, and the two ports 142, 144, engage the bottom surface of the material under test 112. In another embodiment, the top surface 152 of the probe 102-A is coplanar with the top surface 504 of the housing 502-1. In various embodiments with a table 512, the top surface 152 of the probe 102-A protrudes or is coplanar the surface 514 supporting the material under test 112.

The ambient air port 146 is positioned inside the housing 502-1. The fans 506 in the side of the housing 502-1 force air to circulate between the space outside the housing 502-1 and space inside the housing 502-1. In this way, the ambient air port 146 receives ambient air 136 that is at a temperature representative of the volume of air around the probe 102-A. In one embodiment, the opening 516-A in the side of the housing 502-1 holds one fan 506 and the adjacent opening 516-B is a vent that allows passage of ambient air 136 from the action of the fan 506. In various embodiments, the number and location of the openings 516 varies, for example, the housing 502-1 has two fans 506 and multiple vents 516-B.

In the illustrated embodiment, two flow gages 208-R, 208-A are shown on the side of the housing 502-1. The flow gages 208 have an indicator showing the current flow rate and an adjustable flow valve for controlling and setting the flow rate. One flow gage 208-R is in-line with the return air conduit 124 and indicates/controls the return air 134 flow. The other flow gage 208-A is in-line with the ambient air conduit 126 and indicates/controls the ambient air 136 flow. In another embodiment, a flow gage 208-H is in-line with the heated air conduit 122 and indicates/controls the heated air 132 flow. In yet another embodiment, the flow gages 208 are not used and the flow rate is fixed based on the selection of components and tubing.

In the illustrated embodiment, the output 226 for the differential temperature instrument (dT Instr) 108 includes a digital-type indicator 226'. The illustrated digital-type indicator 226' displays the differential temperature. In various embodiments, the differential temperature is displayed as a percent between 0 and 100% for the amount of re-breathing or as a voltage or other value. Next to the indicator 226' is an operator for the zero adjust 424 that allows for zeroing the differential temperature amplifier 224 and output 226.

In the illustrated embodiment, the differential pressure instrument 110' is a dial-type gage that is connected to the return air conduit 124 and the ambient air conduit 126. In this way, the differential pressure between the return air 134 and the ambient air 136 is available to be observed and recorded during testing of the material under test 112.

FIG. 5 also illustrates a platform, or table, 512 that supports the material under test 112 when the material under test 112 is substantially larger than the top surface 504 of the analyzer 100-1. The platform 512 and material under test 112 are partially illustrated in the figure. The platform 512 has a table surface 514 that is coplanar with the top surface 504 of the analyzer housing 502-1. The platform 512 has an opening 516 sized and configured to receive the analyzer housing 502-1 with the top surface 152 of the probe 102-A exposed.

In another such embodiment, the opening 516 in the platform, or table, 512 is circular and sized to receive the probe 102-A in which the probe 102-A is configured to have the top surface 152 flush or slightly proud of the top surface 504 of the table surface 514. In yet another embodiment, the analyzer housing 502-1 is sized to fully support the material under test 114, and in such an embodiment, the platform 512 is not used.

In one embodiment, the material under test 112 is weighted down with a plate 522. The plate 522 includes a series of openings 524 that allow free passage of air between the surrounding space and the material under test 112. In this way, the plate 522 does not adversely affect the results of the re-breathing test by the analyzer 100-1. The plate 522 is useful to ensure that the bottom surface of the material under test 112 maintains contact with the top surface 152 of the probe 102-A. In one such embodiment, the plate 522 is configured to ensure that the bottom surface of the material under test 112 is biased against the top surface 152 of the probe 102-A with a selected force.

Figure 6:
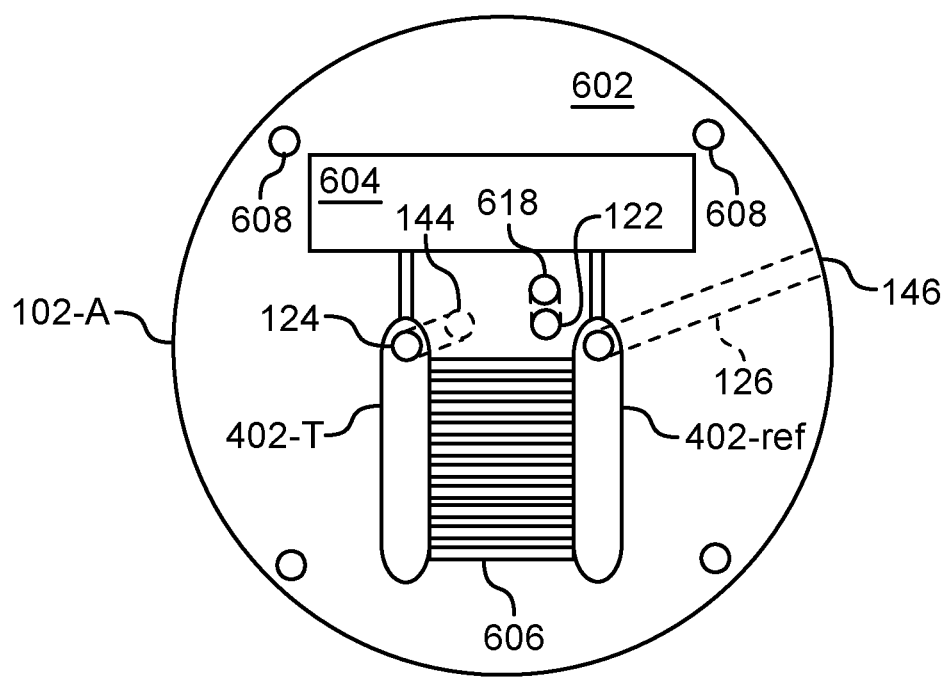
FIG. 6 is a bottom view of a first embodiment of a disc-shaped probe.
Figure 7:
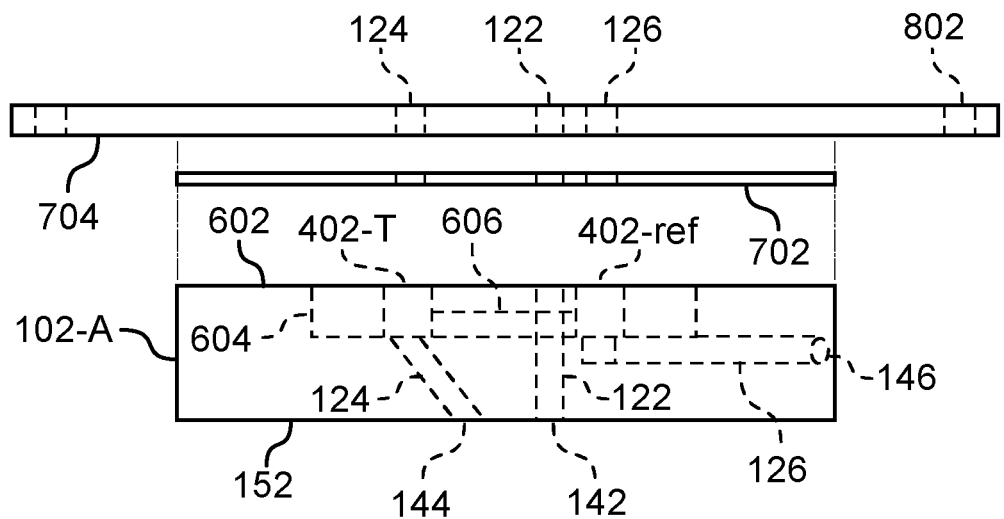
FIG. 7 is a side view of the first embodiment of the disc-shaped probe.
Figure 8:
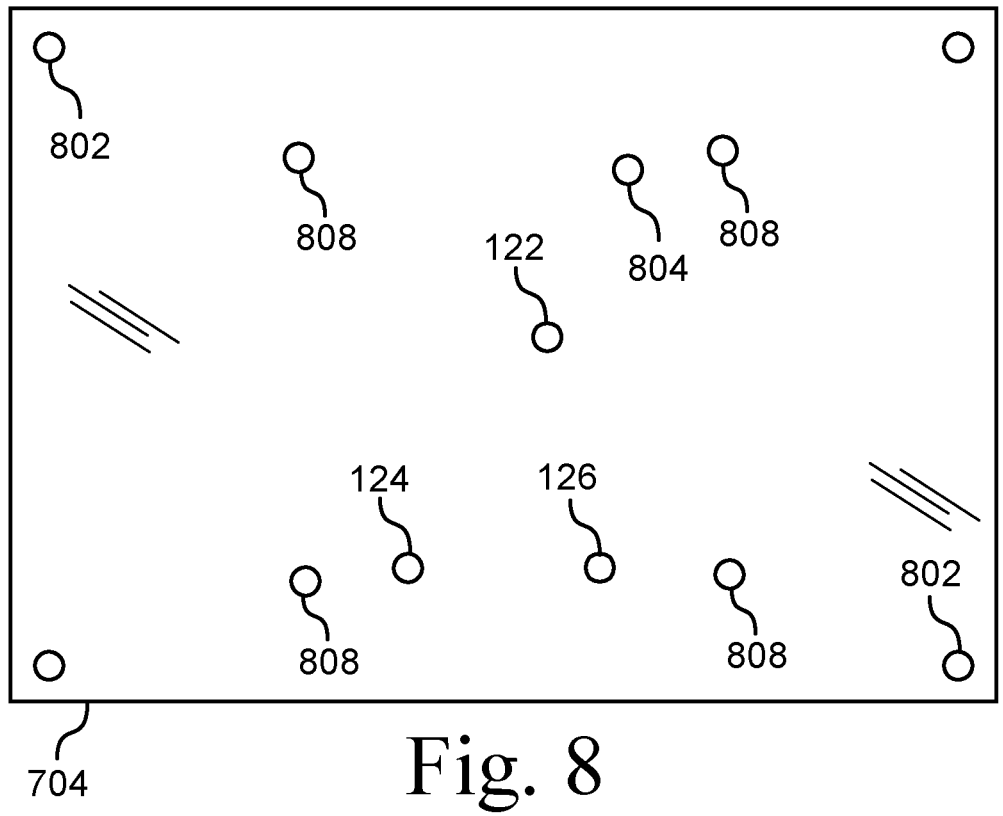
FIG. 8 is a bottom view of one embodiment of a support plate.

FIG. 6 illustrates a bottom view of a first embodiment of a disc-shaped probe 102-A. FIG. 7 illustrates a side view of the first embodiment of the disc-shaped probe 102-A, along with a gasket 702 and a support plate 704. FIG. 8 illustrates a bottom view of one embodiment of a support plate 704. The illustrated probe 102-B has disc-shape, similar to a hockey puck. The illustrated embodiment of the probe 102-A has such a size and shape that the probe 102-A engages the material under test 112 to produce repeatable results because the flat surface 152 avoids variations in orientation of the probe 102 and in the surface of the material under test 112. Also, the size and shape of the probe 102-A is such that it is easily reproduced during manufacturing such that copies of the probe 100-A readily produce repeatable results when testing the same material under test 112.

In the illustrated embodiment, the probe 102-A is configured to hold the thermopile 222' and the amplifier 224. The cavities 402-T, 402-ref in the bottom 602 of the probe are sized and configured to receive the junctions 422-T, 422-ref of the thermopile 222'. In the illustrated embodiment, the cavity 402-T, in conjunction with the port on each end of the cavity 402-T, forms a portion of the return air conduit 124. The junctions 422-T are positioned longitudinally in the cavity 402-T and near the center of the space between the walls defining the cavity 402-T. The junctions 422-T are positioned away from the walls defining the cavity 402-T. In this way, the junctions 422-T are responsive to the return air 134 in the cavity 402-T. In a similar manner, the cavity 402-ref, in conjunction with the port on each end of the cavity 402-ref, forms a portion of the ambient air conduit 126. The junctions 422-ref are positioned longitudinally in the cavity 402-ref and near the center of the space between the walls defining the cavity 402-ref. The junctions 422-ref are positioned away from the walls defining the cavity 402-ref. In this way, the junctions 422-ref are responsive to the ambient air 136 in the cavity 402-ref. Each cavity 402-T, 402-ref has a channel that receives the electrical leads from the thermopile 222'.

Multiple channels 606 are positioned between the cavities 402-T, 402-ref. The thermopile junctions 422-T, 422-ref are in the cavities 402-T, 402-ref and the thermocouple wire joining the junctions 402-T, 402-ref are routed in the channels 606. In one embodiment, to minimize heat transfer between the probe 100 and the thermocouple wire in the channels 606, the channels 606 are filled with an insulating material that is packed around the wire between the junctions 422-T, 422-ref. In one embodiment, to minimize any air leakage between the cavities 402-T, 402-ref, the channels 606 are filled with a sealing material that is packed around the wire between the junctions 422-T, 422-ref. In one such embodiment, the material in the channels 606 provides both insulation and a seal.

In the illustrated embodiment, the cavity 604 is sized and configured to receive the amplifier 224. In one embodiment, the amplifier 224 includes a circuit that receives an input from the temperature sensor 222' and has connections to the zero adjust 424 and the output 226. The gasket 702 and the support plate 704 for the probe 102 includes an opening 804 that allows passage for the wiring connections between the amplifier 224 and the zero adjust 424 and the output 226. In another embodiment, the amplifier 224 is located remote to the probe 102, making the cavity 604 in the probe 102 unnecessary.

The support plate 704 is secured to the bottom 602 of the probe 102 and to a structure inside the housing 502-1. The gasket 702 provides a seal between the support plate 704 and the probe 102. The support plate 704 supports the probe 102 in position relative to the top plate 504 of the housing 502-1. The support plate 704 includes mounting holes 802 that receive fasteners that secure the plate 704 to the structure inside the housing 502-1. The support plate 704 includes mounting holes 808 that receive fasteners that secure the plate 704 to threaded, blind holes 608 in the probe 102-A.

The gasket 702 and the support plate 704 include passageways defining a portion of the heated air conduit 122, the return air conduit 124, and the ambient air conduit 126. The passageways in the gasket 702 and the support plate 704 mate with the corresponding passageways in the probe 102 and are configured to mate with the conduits 122, 124, 124 that extend away from the plate 704 and probe 102-A. In the embodiment in which the heater temperature sensor 218 is positioned at the exhaust port 142, the probe 102 includes a passageway 618 that connects with the heated air conduit 122 proximate the exhaust port 142. The sensor portion of the temperature sensor 218 is positioned at the end of the passageway 618 proximate the exhaust port 142.

In one embodiment in which a temperature controller 114 is associated with the probe 100, the temperature controller 114 directly controls the temperature of the plate 704 and indirectly controls the temperature of the probe 100. In one embodiment of the analyzer 100-A, such as illustrated in FIG. 5, the plate 704 is aluminum or other material with a higher thermal conductivity than the probe 100. In other embodiments, such as one without the temperature controller 114, the temperature of the plate 704 is maintained at ambient air temperature by the fan 506 moving ambient air across and around the plate 704.

Figure 9:
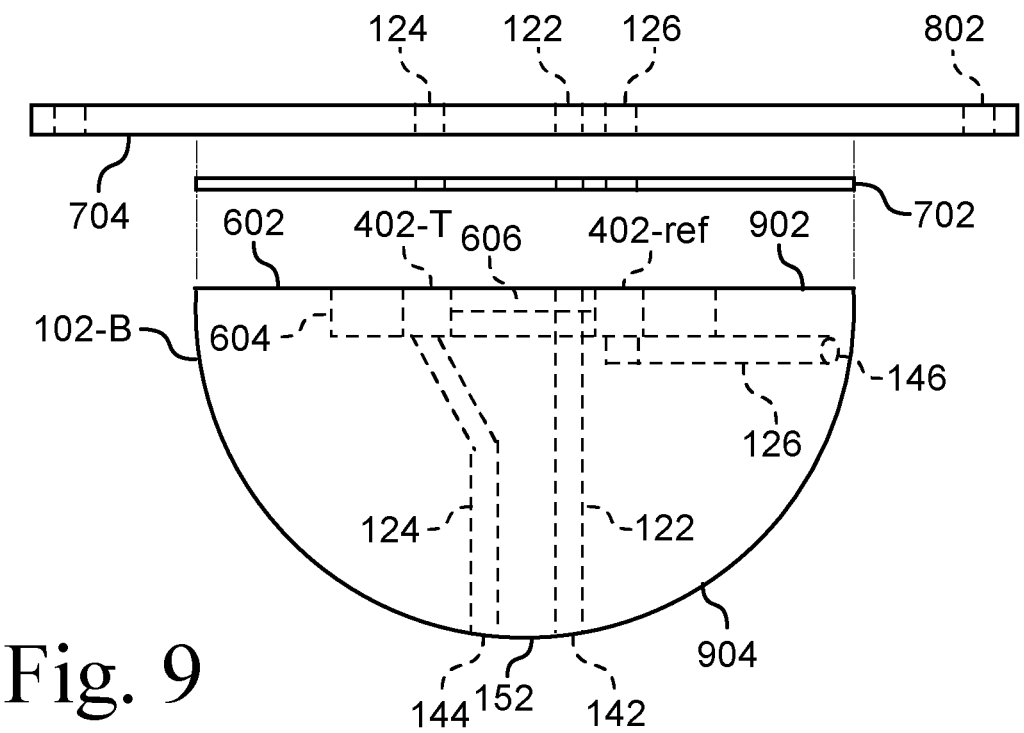
FIG. 9 is a side view of another embodiment of the probe.

FIG. 9 illustrates a side view of another embodiment of the probe 102-B. The illustrated probe 102-B has an ellipsoidal-shape, and like the probe 100-A, includes cavities 402, 606 and passages. In one embodiment, the probe 102 is a manikin head or a portion of a manikin head. Such a probe configuration increases the difficulty in obtaining repeatable test results due to the potential of different orientations relative to the material under test 112. The illustrated embodiment of the probe 102-B has a substantially hemispherical shape where the size and shape of the probe 102-B mimics the overall size and shape of the portion of an infant's face that is pressed against the material under test 112, while also having a shape that is readily reproduced and positioned on the material under test 112 to produce repeatable results.

The illustrated probe 102-B has an inboard end 902 that is circular and an outboard end 904 that has a partial ellipsoidal-shape, that is, the end 904 is defined by a truncated ellipsoid. In one such embodiment, the end 904 has a hemispherical shape. In other embodiments, the end 904 has an ovoid shape.

The illustrated probe 102-B, like the probe 102-A, includes cavities 402, 606 and various passages. The outboard end 904 of the probe 102-B, which forms at least a portion of the outer surface 152, has an exhaust port 142 and an intake port 144 that are each in fluid communication with the air circulator 106. In one embodiment, the temperature sensor 222 is located in the probe 102. In another embodiment, the temperature sensor 222 is located in the conduits 124, 126 outside the probe 102.

Figure 10:
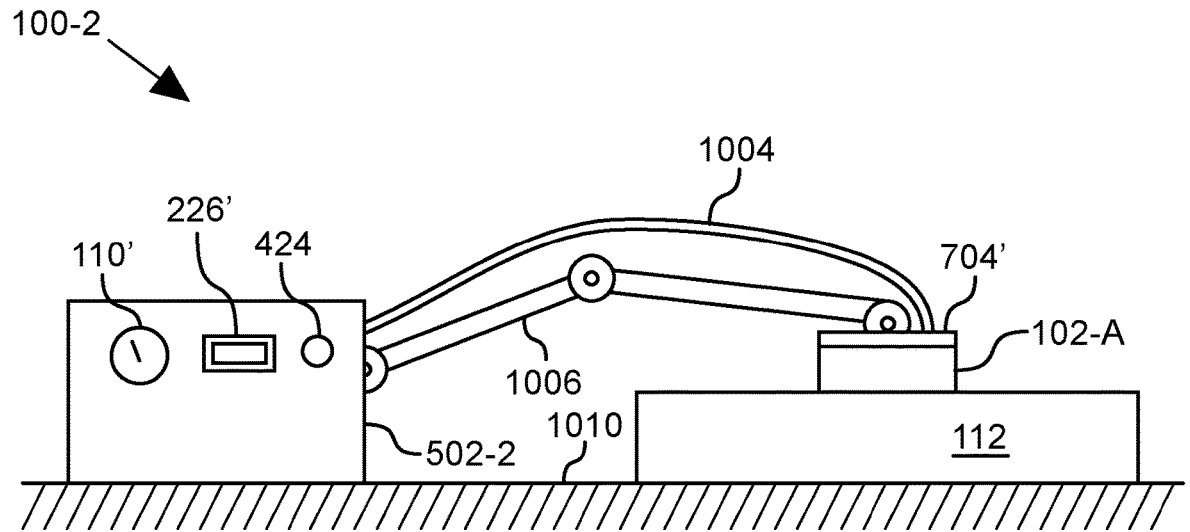
FIG. 10 is a side view of a second embodiment to a re-breathing analyzer.

FIG. 10 illustrates a side view of a second embodiment to a re-breathing analyzer 100-2. The illustrated embodiment of the re-breathing analyzer 100-2 includes a housing 502-2, an umbilical 1004, an articulated arm 1006, and a probe 102-B with a plate 704'.

The housing 502-2 includes the air circulator 106 and heater 104. An articulated arm 1006 is attached to the housing 502-2 with a pivoting joint. The housing also includes a differential pressure gage 110', an output 226', and an operator for the zero adjust 424. In one embodiment, such as one in which the housing 502-2 contains the thermopile 222' with its associated cavities 402-T, 402-ref, the housing 502-2 also includes at least one fan 506 and vents 516. In an embodiment in which the probe 102-A contains the thermopile 222' with its associated cavities 402-T, 402-ref, the housing 502-2 does not need a fan 506 in order to maintain the temperature of ambient air 136 inside the housing 502-2 for the thermopile 222', although such a fan 506 and vent 516-B may be needed for thermal control of the housing internals.

The articulated arm 1006 is configured to allow the probe 102-A to engage the material under test 112. The end of the articulated arm 1006 is pivotably attached to a support plate 704' with an attached probe 102-A. The articulated arm 1006 includes joints that allow the height of the probe 102-A to be adjusted relative to the surface 1010 upon which the housing 502-2 and material under test 112 rest. The mounting plate 704' and probe 102-A have a weight that allows the surface 152 of the probe 102-A to be biased against, or have a selected thrust, the material under test 112 to ensure repeatable tests. In one such embodiment, the weight of the mounting plate 704' and probe 102-A defines the selected force of the probe 102 against the material under test 112.

The analyzer 100-2 includes an umbilical 1004 that extends between the housing 502-2 and the support plate 704' and probe 100-A combination. In an embodiment in which the housing 502-2 contains the thermopile 222' with its associated cavities 402-T, 402-ref, the umbilical 1004 carries the conduits 122, 124, 126 to the ports 132, 134, 136 in the probe 100-A. In an embodiment in which the probe 102-A contains the thermopile 222', the umbilical 1004 carries both the conduits 122, 124, 126 to the ports 132, 134, 136 in the probe 100-A and the electrical connections between the components in the housing 502-2 and the probe 100-A.

Figure 11:
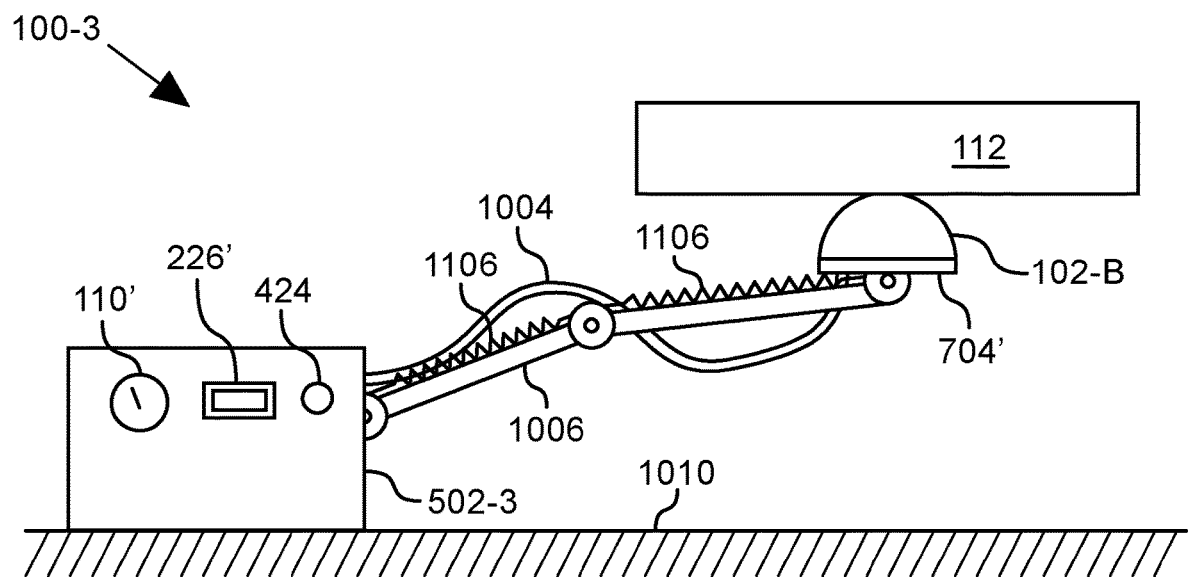
FIG. 11 is a side view of a third embodiment to a re-breathing analyzer.

FIG. 11 illustrates a side view of a third embodiment to a re-breathing analyzer 100-3. The illustrated embodiment is similar to the analyzer 100-2 shown in FIG. 10 except that the probe 100-B has a hemispherical shape such as illustrated in FIG. 9.

FIG. 11 also illustrates that the probe 102-B at the end of the articulated arm 1006 is also configured to engage the material under test 112 when that material 112 is suspended above the probe 100-B. In one embodiment, the articulated arm 1006 biases the probe 102 against the raised material under test 112, thereby ensuring that the ports 142, 144 in the probe 102 are positioned proximate the material under test 112. In one such embodiment, the articulated arm 1006 includes springs 1106 that bias the probe 102 against the material under test 112. In one such embodiment, the springs 1106 compensate for the weight of the mounting plate 704' and probe 102-A and, further, the springs 1016 define the selected force of the probe 102 against the material under test 112.

The re-breathing analyzer 100 includes various functions. The function of determining the degree of re-breathing for a material under test 112 is implemented, in one embodiment, by supplying heated air 132 to the material under test 112 through a probe 100 and receiving return air 134 through the probe 100, where the temperature of the return air 134 corresponds to the amount of re-breathing caused by the material under test 112.

The function of measuring the differential temperature is implemented, in one embodiment, by a differential temperature instrument circuit 108' that includes a thermopile 222' with one set of junctions 422-T in the air stream of the return air 134 from the probe 100 and the opposite, or reference, set of junctions 422-ref in the air stream of ambient air 136. In another embodiment, the function of measuring the differential temperature is implemented by a differential temperature instrument circuit 108 that includes a temperature sensor 222, an amplifier 224, and an output device 226. In one such embodiment, the temperature sensor 222 is a thermocouple. In another such embodiment, the temperature sensor 222 includes one or more sensors that are responsive to temperature, along with a circuit that provides an output corresponding to the temperature difference between two gasses.

The function of interfacing with the material under test 112 is implemented by a probe 102 that has an exhaust port 142 and an intake port 144 positioned to be in close proximity or contact with the material under test 112 when a test is being conducted. In one such embodiment, the probe 102-A has a disc-shape, that is, it is cylindrical with the diameter being greater than the distance between the two ends 152, 602. In another such embodiment, the probe 102-B has one end 902 that is circular and an opposite end 904 that has an ellipsoidal-shape. In one such embodiment, the end 904 is hemispherical-shaped. In various embodiments, the probe 102 and the material under test 112 are forced together with a selected bias or thrust therebetween. In one such embodiment, the probe 102 is biased or thrust against the material under test 112, such as by the probe's weight as shown in FIG. 10 or by springs 1106 having a spring bias forcing the probe 102 against the material under test 112. In another such embodiment, the probe 102 and the material under test 112 are forced together by the material under test 112 having a selected bias or thrust against the probe 102, such as illustrated in FIG. 5, either by the weight of the material under test 112 or with the plate 522 applying a weight to the material under test 112. In one example, the selected bias is a force of 10 Newtons applied over the surface 152 of the probe 102 in contact with the material under test 112.

The function of indicating re-breathing of the material under test 112 is implemented, in one embodiment, by the output 226 of the differential temperature instrument 108. In various embodiments, the output 226 displays, transmits, and/or records the differential temperature of the return air 134 relative to a reference, such as ambient air 136 or the heated air 132.

The function of minimizing calibration of the analyzer 100 is implemented, in one embodiment, by using a thermocouple or thermopile 222' with a fixed gain amplifier 224. The type of thermocouple wire used for the temperature sensor 222 defines the voltage per degree of temperature. In one embodiment, a Type E thermocouple is used because it provides a higher output than many other types. The use of a thermopile 222' with multiple pairs of junctions 422-T, 422-ref increases the output level and the resolution of the differential temperature measurement signal between the junctions 422-T, 422-ref.

From the foregoing description, it will be recognized by those skilled in the art that a re-breathing analyzer 100 has been provided. The re-breathing analyzer 100 determines the presence and amount of re-breathing associated with a material under test 112. The analyzer 100 includes an air circulator 106 that causes air to move to and from a probe 102 that is the interface between the analyzer 100 and the material under test 112. A heater 104 supplies heated air 132 to an exhaust port 142 on the face 152 of the probe 102. An intake port 144 adjacent to the exhaust port 142 on the face 152 of the probe 102 receives return air 124 that is drawn in by the air circulator 108. In one embodiment, a differential temperature instrument 108 measures the temperature difference between the return air 134 and the ambient air 136.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for analyzing re-breathing of bedding material, said apparatus comprising:

an air circulator having an output in fluid communication with a first conduit, said air circulator having a first input in fluid communication with a second conduit, and said air circulator having a second input in fluid communication with a third conduit;

a heater associated with said first conduit, said heater configured to raise a temperature of a gas in said first conduit;

a probe with a surface configured to engage a material under test, said probe having an exhaust port and a first intake port on said surface, said exhaust port proximate said first intake port, said exhaust port in fluid communication with said first conduit, said first intake port in fluid communication with said second conduit, said third conduit having a distal end receiving ambient air proximate said probe; and a differential temperature measuring device including a temperature sensor, an amplifier, and at least one output device, said temperature sensor being a thermopile with a set of first junctions in fluid communication with said second conduit and a set of second junctions in fluid communication with said third conduit whereby said thermopile is responsive to a differential temperature of gas flowing through said second and third conduits.

2. The apparatus of claim 1 wherein said air circulator includes an air pump, a discharge of said air pump in fluid communication with said first conduit, a pump intake of said air pump in fluid communication with said second and third conduits.

3. The apparatus of claim 1 wherein said air circulator includes an air cylinder with a reciprocating actuator that causes said air cylinder to repeatedly move air into and out of said air cylinder, said air cylinder in fluid communication with a first check valve configured to allow air to flow into said first conduit from said air cylinder, said air cylinder in fluid communication with a second check valve configured to allow air to flow from said second conduit into said air cylinder, whereby said air cylinder operates as a mechanical lung.

4. The apparatus of claim 3 wherein said air cylinder is in fluid communication with said second check valve configured to allow air to flow from said third conduit into said air cylinder, whereby air in said second and third conduits flow into said air cylinder at the same time.

5. The apparatus of claim 1 wherein said surface of said probe has a partial ellipsoidal-shape.

6. The apparatus of claim 1 wherein said probe has a cylindrical, disc-shape.

7. The apparatus of claim 1 wherein said first set of junctions are disposed in a first cavity in fluid communication with said second conduit, and said second set of junctions are disposed in a second cavity in fluid communication with said third conduit.

8. The apparatus of claim 7 wherein said first and second cavities are disposed in said probe.

9. The apparatus of claim 7 wherein said first and second cavities are disposed in said probe, and said amplifier is disposed in a third cavity in said probe.

10. The apparatus of claim 1 wherein said amplifier is a fixed gain amplifier.

11. The apparatus of claim 1 wherein said amplifier includes a zero adjust whereby an output signal of said amplifier is adjustable to a zero point.

12. An apparatus for analyzing re-breathing associated with a material under test, said apparatus comprising:

an air pump with a discharge in fluid communication with a first conduit, said first conduit being terminated at an exhaust port, said air pump having an air intake in fluid communication with a second conduit, said second conduit being terminated at a first intake port;

a heater associated with said first conduit, said exhaust port discharging heated air;

a probe having a surface configured to engage the material under test, said exhaust port and said first intake port disposed on said surface, said exhaust port proximate said first intake port;

a temperature sensor responsive to a return air temperature in said second conduit; and an output device responsive to a temperature measurement from said temperature sensor.

13. The apparatus of claim 12 wherein said probe has a cylindrical, disc-shape.

14. The apparatus of claim 12 further including a third conduit in fluid communication with said air intake of said air pump, said third conduit being terminated at a second intake port positioned proximate said probe, wherein said third conduit carries ambient air to said air pump.

15. The apparatus of claim 14 wherein said temperature sensor is a thermocouple with at least one first junction located in a first cavity in fluid communication with said second conduit, said thermocouple with at least one second junction located in a second cavity in fluid communication with said third conduit, whereby said thermocouple is responsive to a differential temperature between a return air temperature in said second conduit and an ambient air temperature in said third conduit.

16. The apparatus of claim 12 further including a housing having a surface with an opening through which said surface of said probe is exposed and accessible to the material under test; and said air pump and said heater disposed inside said housing.

17. The apparatus of claim 12 wherein said probe is disposed partially in a housing with said surface of said probe exposed through an opening in a top surface of said housing; said surface of said probe protruding through said opening in said top surface of said housing; and said air pump, said heater, and said first, second, and third conduits disposed inside said housing.

18. The apparatus of claim 12 further including a housing and an articulated arm, said articulated arm having a first end attached to said housing, said articulated arm having a send end pivotably attached to said probe whereby said probe is movable relative to said housing, said housing enclosing said air pump and said heater.

19. An apparatus for analyzing re-breathing associated with a material under test, said apparatus comprising:

an air pump with a discharge in fluid communication with a first conduit, said first conduit being terminated at an exhaust port, said air pump having an air intake in fluid communication with a second conduit, said second conduit being terminated at a first intake port, said air pump having a third conduit in fluid communication with said air intake of said air pump, said third conduit being terminated at a second intake port;

a heater associated with said first conduit, said exhaust port discharging heated air;

a probe having a surface configured to engage the material under test, said exhaust port and said first intake port disposed on said surface, said exhaust port proximate said first intake port, said second intake port positioned proximate said probe;

a differential temperature measuring device including a temperature sensor, an amplifier, and at least one output device, said temperature sensor being a thermopile with a set of first junctions disposed in a first cavity in fluid communication with said second conduit and a set of second junctions disposed in a second cavity in fluid communication with said third conduit whereby said thermopile is responsive to a differential temperature of air flowing through said second and third conduits, said amplifier having a fixed gain.

20. The apparatus of claim 19 wherein said first and second cavities are disposed in said probe.

* * * * *